(12) United States Patent
Okada et al.

(10) Patent No.: US 6,664,283 B1
(45) Date of Patent: Dec. 16, 2003

(54) PHARMACEUTICALS FOR NEUROGENIC PAIN

(75) Inventors: Masamichi Okada, Ibaraki (JP); Yukinori Nagakura, Ibaraki (JP); Tetsuo Kiso, Ibaraki (JP); Takashi Toya, Ibaraki (JP); Satoshi Hayashibe, Ibaraki (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/031,404

(22) PCT Filed: Aug. 1, 2000

(86) PCT No.: PCT/JP00/05074

§ 371 (c)(1),
(2), (4) Date: May 15, 2002

(87) PCT Pub. No.: WO01/08705

PCT Pub. Date: Feb. 8, 2001

(30) Foreign Application Priority Data

Aug. 2, 1999 (JP) .............................. 11/218309

(51) Int. Cl.$^7$ ...................... A61K 31/415; A61K 31/38; C07D 513/02
(52) U.S. Cl. ...................... 514/397; 514/396; 514/394; 514/393; 514/385; 514/438; 514/439; 514/443; 514/444; 548/151; 548/303.1; 548/150; 548/302.1; 548/302.4; 548/302.7; 548/301.7
(58) Field of Search ................................. 514/385, 393, 514/396, 397, 438, 439, 443, 444, 394; 548/151, 303.1, 150, 302.1, 302.4, 302.7, 301.7

(56) References Cited

PUBLICATIONS

Marian E. Fundytus, et al., "In vivo antinociceptive activity of anti–rat mGluR$_1$ and mGluR$_5$ antibodies in rats," NeuroReport, Mar. 1998, pp. 731–735, vol. 9, No. 4, Rapid Science Publishers.

Marie R. Young, et al., "Antisense Ablation of Type I Metabotropic Glutamate Receptor mGluR$_1$ Inhibits Spinal Nociceptive Transmission," Journal of Neuroscience, Dec. 1998, pp. 10180–10188, vol. 18, No. 23, New York, NY.

T.E. Salt, et al., "Antagonism of Metabotropic Glutamate Receptor–Medidated Responses and Nociceptive Responses by the mGluR1–Selective Antagonist LY367385 in the Rat Thalamus," British Journal of Pharmacology, 1998, pp. 15P, Vol 123.

Lee J. Martin, et al. "Cellular Localization of a Metabotropic Glutamate Receptor in Rat Brain" Neuron, vol. 9, 259–270, Aug. 1992.

Peter Holzer "Capsaicin: Cellular Targets, Mechanisms of Action, and Selectivity for Thin Sensory Neurons" Pharmacological Reviews, vol. 43, No. 2, 143–201, 1991.

Salt, T.E. et al., "The Function of Metabotropic Excitatory Amino Acid Receptors in Synaptic Transmission in the Thalamus: Studies with Novel Phenylglycine Antagonists", Neurochem. Int. vol. 24, No. 5, pp. 451–458, 1994.

Fisher, Kim et al., "Intrathecal administration of the mGluR compound, (S)–4CPG, attenuates hyperalgesia and allogynia associated with sciatic nerve constriction injury in rats", International Association for the Study of Pain, Pain 77 (1998) pp. 59–66.

Fundytus, Marian E. et al., "In vivo antinociceptive activity of anti–rat mGluR$_1$ and mGluR$_5$ antibodies in rats", Rapid Science Publishers, vol. 9, No. 4, Mar. 9, 1998, pp. 731–735.

Neugebauer, Volker et al., "Role of Metabotropic Glutamate Receptor Subtype mGlu R1 in Brief Nociception and Central Sensitization of Primate STT Cells", The American Physiological Society, 1999, 272–282.

*Primary Examiner*—Theodore J. Criares
*Assistant Examiner*—S. Jiang
(74) *Attorney, Agent, or Firm*—Sughrue Mion, PLLC

(57) ABSTRACT

This invention relates to pharmaceuticals for neuropathic pains comprising an mGluR1 receptor antagonist for systemic administration. Drugs efficacious in treating various neuropathic pain can be provided by the invention.

4 Claims, 2 Drawing Sheets

PHARMACEUTICALS FOR NEUROGENIC PAIN

This application, is a 371 of PTC/JP00/05074.

TECHNICAL FIELD

This invention relates to novel medical uses as pharmaceuticals for neuropathic pain by systemically administrating a compound having an mGluR1 receptor antagonistic activity.

BACKGROUND OF THE INVENTION

Neuropathic pain is intractable pain caused as a result of a functional abnormality of the peripheral or central nervous system. Neuropathic pain manifests itself due to neurological disorders accompanying various causes such as wound, infection, cancer, ischemia and metabolic disorders including diabetes mellitus. Though there are many unclear points on the mechanism of neuropathic pain, it is considered that abnormal continuous firing of sensory nerve and the like are the cause. Typical symptoms of neuropathic pain include allodinia, hyperalgesia, hyperesthesia and the like. Their symptoms include characteristic pains expressed as "like burning", "like stinging", "like electrical shock" and the like. It is known that analgesics, particularly narcotic analgesics and the like, which are effective for general nociceptive pains are hardly effective for neuropathic pain (*The Lancet*, 353, 1959–1966, 1999). For example, it is known that morphine has a strong analgesic effect on nociceptive pains but does not show a sufficient effect on neuropathic pain. Consequently, this resistance to morphine is used in diagnoses as a main characteristic of neuropathic pain (*Advances in Medical Science*, 189(10), 751–755, 1999). It is considered that the ineffectiveness of morphine for neuropathic pain is due to degeneration of inhibitory neurons and reduction of opiate receptors caused by neurological changes of nerves (Recent Brain and Neuroscience Series vol. 6, Neuroscience of Pains, published by Medical View, p. 97, 1997).

Accordingly, it is considered that various factors are complicatedly involved in the generation and maintenance of neuropathic pain. As the therapeutic methods, neurosurgery treatments such as nerve block and epidural spinal cord electric stimulus (*Advances in Medical Science*, 189 (10), 757–762, 1999), tricyclic antidepressants (*Clinical and Drug therapies*, 18 (7), 643–646, 1999), intrathecal administration of baclofen (*Functional Cerebral Nerve Surgery*, 33, 45–49, 1994) and the like have so far been used. However, since a safe and effective therapeutic method has not been established, concern has been directed toward the development of a therapy effective for neuropathic pain.

Glutamate is a main excitatory transmitter that is present in sensory nerve fibers and mediates sensory information to the spinal cord. Peripherally evoked nociceptive signals are sent to supraspinal regions through non-NMDA, NMDA and mGluRs in the spinal cord. Also, it has been reported that NMDA receptor antagonists and AMPA receptor antagonists improve reduced pain thresholds in a neuropathic pain model (*Br. J. Pharmacol.*, 122, 1478–1482, 1997). Based on the above, it is considered that in the spinal cord glutamate may be released excessively in the state of neuropathic pain.

On the other hand, the following reports have been published on the involvement of mGluRs in neuropathic pain.

Reference 1 (*Neuroreport*, 9, 731–735, 1998) reported that intrathecally administered antibodies for mGluR1 and mGluR5 before and 24 hours after surgical operation inhibited a development of cold hyperalgesia but did not inhibit a development of mechanical allodynia in rats.

Reference 2 (*Pain*, 77, 59–66, 1998) reported that intrathecal treatment (twice-daily injections on post-operative days 0–8) of a Group I antagonist ((S)-4CPG: (S)-4-carboxyphenylglycine) attenuated cold hyperalgesia on the post-operative days 4 and 8. But it did not have an effect on that on the post-operative days 12 and 16. In addition, it also inhibited a development of mechanical allodynia on the post-operative days 4 and 8, but it did not have an effect on that on the post-operative days 12 and 16. On the other hand, twice-daily intrathecal injections of (S)-4CPG on post-operative days 8–11 did not inhibit development of lowered pain threshold at any day of the test. Therefore, it was discussed that Group I mGluRs are involved in the development, and not the maintenance, of mechanical allodynia and cold hyperalgesia.

The authors of the references 1 and 2 have confirmed prophylactic effects of the intrathecal administration of mGluR1/5 antagonist and antibody for mGluR1 in nerve ligation-induced neuropathic pain animal models. However, since the reference 2 has concluded that mGluR1/R5 antagonist did not improve the well-established mechanical allodynia or cold hyperalgesia, it has been considered that mGluR1 and/or mGluR5 antagonist has an prophylactic effect, which means the prevention of pain threshold reduction after nerve injury, but does not have a therapeutic effect, which means improving lowered pain thresholds to the normal level.

In addition, these references 1 and 2 neither disclose nor suggest the therapeutic effect of systemically administered mGluR1 antagonist on neuropathic pain.

In these references 1 and 2, intrathecal administration is used for the evaluation of drugs in neuropathic pain models. Since it is known that mGluR1 receptor is involved in the nociceptive signaling in the spinal cord, it is likely that the mGluR1/R5 antagonists and antibody for mGluR1 were intrathecally administered in the references 1 and 2. However, these mGluR1/R5 antagonists and antibody for mGluR1 did not show the therapeutic effect on neuropathic pain even by their intrathecal administration, which is thought to be the most efficient administration route to deliver drugs to the action sites.

On the other hand, it has been reported that the mGluR1 receptor is highly expressed in the thalamus and exists particularly on relay neurons in the thalamus, which transmit noxious signals to the cerebral cortex (*Neuron*, 9, 259–270, 1992; *Neurochem. Int.* 24, 451–458, 1994).

Therefore, the present inventors have considered that it is necessary to block mGluR1 in the thalamus in addition to mGluR1 in the spinal cord to obtain a sufficient therapeutic effect for neuropathic pain, and have attempted to evaluate the therapeutic effect of mGluR1 antagonists in neuropathic pain models by systemic administration.

The relationship between mGluR1 in thalamus and neuropathic pain has not been known, and there has been no suggestion from which the therapeutic effect of an mGluR1 antagonist on neuropathic pain by its systemic administration can be predicted.

DISCLOSURE OF THE INVENTION

The object of the invention is to provide excellent systemically active pharmaceuticals for treatment of neuropathic pain.

With the aim of achieving this object, the inventors have conducted studies based on our own ideas and found that an mGluR1 antagonist has therapeutic effects in various neuropathic pain models, thereby accomplishing the invention. STZ (streptozotocin)-induced diabetic mice are used as a neuropathic pain model in which the pain is induced by diabetes-related neurological disorders, and spinal L5/L6 nerve-ligated rats are used as a neuropathic pain model in which the pain is induced by a compression-induced nerve damage (*Pain*, 50, 355–363, 1992). When the effect of the mGluR1 antagonists on lowered pain thresholds by their systemic administration was examined using these models, it was found that the mGluR1 antagonists have an effect which cannot be predicted from the technical levels so far known, namely that the mGluR1 antagonist significantly recovers lowered pain thresholds in these models (therapeutic effect).

The present invention makes it possible to provide pharmaceuticals for neuropathic pain, which are easy for patients to take and have an efficient therapeutic effect with less side effects.

Particularly, the invention relates to the following items.

A pharmaceutical composition for systemic administration for use in treating a neuropathic pain, which contains a compound having mGluR1 antagonistic activity in an amount effective for improving the neuropathic pain and a pharmaceutically acceptable carrier; preferably, the pharmaceutical composition wherein the neuropathic pain is a neuropathic pain induced by diabetes or compression of nerves;

more preferably, the pharmaceutical composition wherein the neuropathic pain is a neuropathic pain induced by diabetes; and more preferably, the pharmaceutical composition wherein the systemic administration method is oral administration.

Further preferably, the pharmaceutical composition wherein the compound having mGluR1 antagonistic activity is a compound having sufficient mGluR1 antagonistic activity for expressing neuropathic pain improving effect by systemic administration; and most preferably, a pharmaceutical for neuropathic pain, wherein the compound having mGluR1 antagonistic activity is a compound selected from 6-amino-N-cyclohexyl-N, 3-dimethylthiazolo[3,2-a]benzoimidazole-2-carboxamide dihydrochloride and (+)-(1R,2S)-6-amino-N-methyl-N-(2-methylcyclohexyl)thiazolo[3,2-a]benzoimidazole-2-carboxamide dihydrochloride.

It also relates to the pharmaceuticals for neuropathic pain, wherein the compound having mGluR1 antagonistic activity is a compound having an activity of 0.1 $\mu$M or less as an $IC_{50}$ value for the PI formation induced by 100 $\mu$M of glutamate.

The following describes the invention further in detail.

The neuropathic pain means an abnormal state of pain sensation, in which a reduction of pain threshold and the like are continued, due to functional abnormalities accompanying damage or degeneration of a nerve, plexus or perineural soft tissue, which is caused by wound, compression, infection, cancer, ischemia and the like, or metabolic disorders such as diabetes mellitus and the like. Illustratively, allodinia (a pain sensation induced by mechanical or thermal stimulus that does not normally provoke pain), hyperalgesia (an excessive response to a stimulus that is normally painful) and hyperesthesia (an excessive response to a contact stimulus) are included in neuropathic pain, though not limited thereto.

Illustrative examples of the neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine.

The neuropathic pain includes the pain caused by either central or peripheral nerve damage. And it includes the pain caused by either mononeuropathy or polyneuropathy.

The therapeutic effect means relieving patients from a neuropathic pain by administering a drug after nerve injury, more illustratively, treating the pain by raising lowered pain thresholds to normal level.

The systemic administration means a route of administration by which a drug is transferred into systemic circulation so that the drug can be distributed to the whole body, particularly to the brain, and its examples include oral administration, intravenous administration, rectal administration, intramuscular administration, subcutaneous administration, sublingual administration and the like.

The compound having sufficient mGluR1 antagonistic activity for therapeutic effect on neuropathic pain by systemic administration means a compound that shows the therapeutic effect on neuropathic pain by systemically administrating the compound to the patient who diagnosed as presenting with symptoms of neuropathic pain or neuropathic animals. Even in the case of compounds which have mGluR1 antagonistic activity, a compound which does not have therapeutic effect on neuropathic pain at a substantially systemic-administrative amount is not included in the invention. Preferred is a compound having an activity as an $IC_{50}$ value for PI formation induced by 100 $\mu$M glutamate, preferably an $IC_{50}$ value calculated by the method described in the following Test Example 1, of high activity than 0.1 $\mu$M, more preferred is a compound having the activity of 60 nM or less.

The effective amount to treat neuropathic pains by systemic administration means substantially systemic administrable amount of the compound having sufficient activity to show treatment effect of neuropathic pain. The dose of each compound is decided by taking into consideration severity of symptoms, pharmacokinetic profile of the drug, administration route, subject to be administered, its age, sex and so on.

Regarding the compound having mGluR1 antagonistic activity as the active ingredient of the pharmaceuticals for neuropathic pain of the invention, its structure is not limited and it may be either a peptide compound or a non-peptide compound, with the proviso that it is a compound which shows mGluR1 antagonistic activity and has sufficient therapeutic activity for neuropathic pain by systemic administration.

The compounds described in the following references or patents can be cited as examples of such mGluR1 antagonist, of which compounds having mGluR1 antagonistic activity and the therapeutic activity for neuropathic pain by systemic administration are included in the invention.

Japanese Patent Laid-Open No. JP08-169884, Japanese Patent Laid-Open No. JP11-189596, Japanese Patent Application No. JP2000-102893, WO 96/15100, WO 95/25110, WO 98/06724, WO 99/26927, WO 99/44639 and the like.

Referring to the synthesis methods described in these documents can produce these compounds.

The pharmaceutical preparation which contains one or two or more of the compounds or salts thereof to be used in the invention as the active ingredient is prepared using carriers, fillers and other additives which are generally used in pharmaceutical preparation.

The carriers and fillers for the pharmaceutical preparation may be either solid or liquid, and their examples include lactose, magnesium stearate, starch, talc, gelatin, agar, pectin, acacia, olive oil, sesame oil, cacao butter, ethylene glycol and the like, as well as other generally used materials.

The administration may be either oral administration by tablets, pills, capsules, granules, powders, solutions and the like, or parenteral administration by injections for use in intravenous, intramuscular or the like injection, suppositories, percutaneous preparations and the like. Clinical dose is optionally decided by taking into consideration symptoms and age, sex and the like of each patient to be treated, but is within the range of generally. from 1 to 1,000 mg, preferably from 50 to 200 mg, per day per adult by oral administration, by dividing the daily dose into 1 to several doses per day, or within the range of from 1 to 500 mg per day per adult by intravenous administration, by dividing the daily dose into 1 to several doses per day, or it is continuously administered into a vein within the range of from 1 hour to 24 hours per day. Since the dose varies under various conditions as described in the foregoing, a smaller dose than the above range may be sufficient enough in some cases.

As the solid composition for use in the oral administration according to the invention, tablets, powders, granules and the like are used. In such a solid composition, one or more active substances are mixed with at least one inert diluent such as lactose, mannitol, glucose, hydroxypropylcellulose, microcrystalline cellulose, starch, polyvinyl pyrrolidone or magnesium aluminummetasilicate. In the usual way, the composition may contain other additives than the inert diluent, such as a magnesium stearate or the like lubricant, calcium carboxymethylcellulose or the like disintegrator, lactose or the like stabilizing agent and glutamic acid, aspartic acid or the like solubilization agent. If necessary, tablets or pills may be coated with a sugar coating or a gastric or enteric coating such as sucrose, gelatin, hydroxypropylcellulose, hydroxypropylmethylcellulose phthalate or the like.

The liquid composition for oral administration use includes pharmaceutically acceptable emulsions, solutions, suspensions, syrups, elixirs and the like and contains a generally used inert diluent such as purified water or ethyl alcohol. In addition to the inert diluent, this composition may also contain a moistening agent, a suspendion and the like adjuvants, as well as sweeteners, flavors, aromatics and antiseptics.

The injections for parenteral administration include aseptic aqueous or non-aqueous liquid, suspensions and emulsions. Examples of the solutions and the suspensions for use in the aqueous liquid include distilled water for injection and physiological saline. Examples of the solutions and the suspensions for use in the non-aqueous liquid include propylene glycol, polyethylene glycol, olive oil or the like plant oil, ethanol or the like alcohol, Polysorbate 80 and the like. Such a composition may further contain adjuvant such as an antiseptic, a moistening agent, an emulsifying agent, a dispersing agent, a stabilizing agent (e.g., lactose) and a solubilization assisting agent (e.g., glutamic acid or aspartic acid). These compositions are sterilized, e.g., by filtration through a bacteria retaining filter, blending of a germicide or irradiation. Alternatively, they may be used by firstly making into sterile solid compositions and dissolving them in sterile water or a sterile solvent for injection use prior to their use.

BEST MOD FOR CARRYING OUT THE INVENTION

Figure 1:
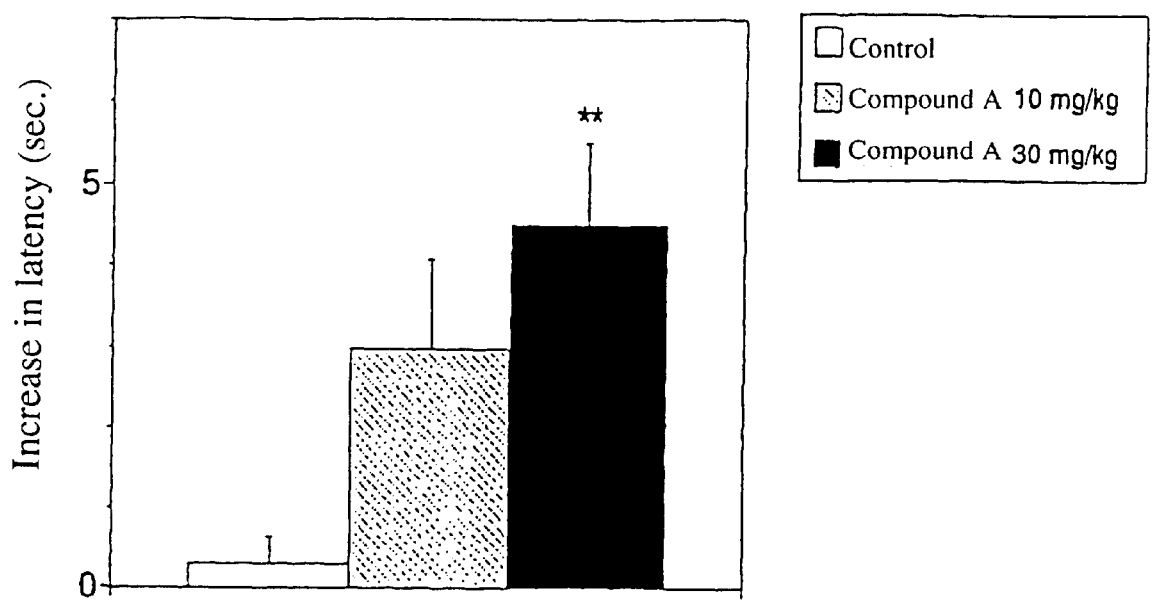
FIG. 1 is a graph showing a reaction latency prolonging effect when a compound A (FIG. A) or a compound B (FIG. B) was administered to STZ-induced diabetes mice.
Figure 1:
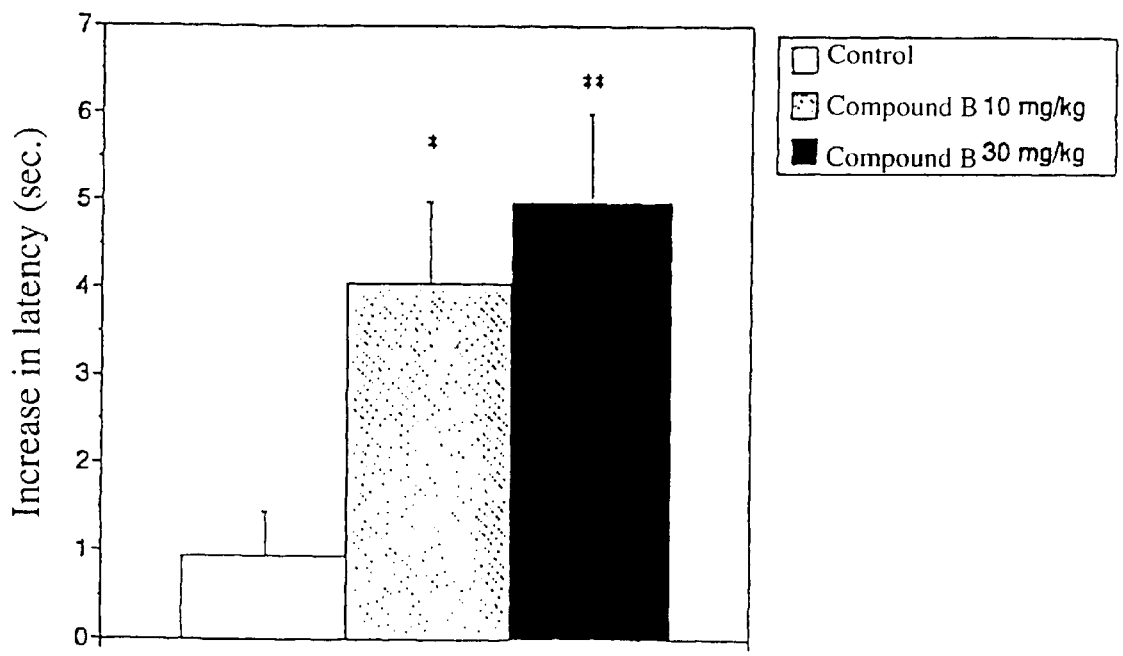

Next, the invention is described further in detail with reference to examples, but the invention is not limited to these examples.

EXAMPLE

Production of Tablets

Tablets were produced using the following components.

| Components | Amount (mg/tablet) |
|---|---|
| Compound A | 200 |
| Cellulose (microcrystalline) | 400 |
| Silicon dioxide (fume) | 10 |
| Stearic acid | 5 |
| Total | 615 mg |

By mixing and compressing these components, tablets each having 615 mg in weight were formed.

The action of the invention to improve lowered pain thresholds in neuropathic animals was evaluated and confirmed in the following manner.

Test Example 1

The mGluR1 receptor antagonistic activity of the compounds used in the invention was confirmed by two test methods.
(Test Compounds)

The following tests were carried out using compound A (6-amino-N-cyclohexyl-N, 3-dimethylthiazolo[3,2-a] benzoimidazole-2-carboxamide dihydrochloride) and compound B ((+)-(1R,2S)-6-amino-N-methyl-N-(2-methylcyclohexyl)thiazolo [3,2-a]benzoimidazole-2-carboxamide dihydrochloride).

1. Measurement of mGluR1 Antagonistic Activity Using Cerebellar Granule Cells
(Cell Culture)

The whole brain was removed from each of seven Wistar rats of 7 to 8 days of age after birth (Japan S L C), and then the cerebellum was isolated in an L-15 medium (Gibco) under a stereoscopic microscope. The isolated cerebellum was cut into pieces using a surgical knife and incubated at 37° C. for 15 minutes in 0.25% trypsin solution (Gibco) containing 750 U/ml of DNase I (Sigma). After termination of the enzyme reaction by adding fetal calf serum (JRH Biosciences), the tissue pieces were centrifuged and the supernatant was removed by sucking. After adding 10 ml of a high potassium medium, cells were dissociated by 5 to 6 times passage through a plastic pipette. After filtering the cell dispersion through a nylon mesh (40 μm pore), viable cells were counted. The cells were diluted in the high potassium medium and then seeded at a density of $8 \times 10^5$ cells/well onto 24-well culture plates (Sumitomo Bakelite) precoated with poly-L-lysine. The cells were cultured at 37° C. under a condition of 5% $CO_2$-95% air.

High potassium medium: BME (Gibco)+10% immobilized fetal calf serum+25 mM KCl+1% penicillin/streptomycin (Gibco)

(Phosphatidylinositol (PI) Hydrolysis Assay)

The PI hydrolysis was measured as described by Aramori et al(*Neuron*, 8, 757–765, 1992). Cerebellar granule cells were cultured for 2 days and then the cells were labeled with myo-[$^3$H]inositol (final 3 µCi/ml) at 37° C. overnight. The cells were incubated for 20 minutes in PBS-LiCl solution and then incubated for 20 minutes in PBS-LiCl solution containing each compound. The reaction was terminated by 0.2 M PCA and the solution was stood at 4° C. for 1 to 2 hours. After adding 2 N KOH and 100 mM EDTA-2Na solution, the plate was centrifuged (2,000 rpm, 5 minutes). The supernatant (1 ml) was applied to Bio-Rad AG1-X8 column, washed with GPI solution (5 mM disodium tetraborate, 60 mM sodium formate) and then eluted with 4 ml of IP3 solution (0.1 M formate, 1 M ammonium formate). The eluate was mixed with a liquid scintillator (Aquasol-2) and the radioactivity in the eluate was determined by a liquid scintillation spectrometer.
(Results)

The $IC_{50}$ value of compound A was 22 nM. Also, the $IC_{50}$ value of compound B was 2.0 nM.

Thus, it was confirmed that both compounds to be used in the invention are potent mGluR1 antagonists.

The following experiments were carried out to confirm these data obtained from above experiment 2. Measurement of inhibition activity by mGluR1 α expression cell
(Cell Culture)

The NIH3T3 cell lines expressing individually mGluR1 α and mGluR5a were cultured using DMEM containing 10% dialyzed fetal calf serum and 100 units/ml, 0.1 mg/ml of streptomycin sulfate. The CHO cell lines expressing individually mGluR2, R4, R6 and R7 were cultured using DMEM containing 10% dialyzed fetal calf serum, 100 units/ml, 0.1 mg/ml of streptomycin sulfate and 2 mM glutamine.
(Measurement of Intracellular Calcium Concentration)

Intracellular calcium concentration of the mGluR5a-expressed cells was measured using a spectrofluorometer as described previously (*Nature*, 383, 89–92, 1996).
(PI Hydrolysis Assay)

Using the mGluR1 α-expressed cells labeled with $^3$H-inositol, hydrolysis of phosphatidylinositol was measured as described previously(*Nature*, 383, 89–92, 1996).
(Measurement of Intracellular cAMP)

Using cell lines expressing individually mGluR2, R6 and R7, cAMP formation after forskolin stimulation in the presence of IBMX was measured using a cAMP assay kit as described previously (*Neuron*, 8, 169–179, 1992).
(Results)

Compound A did not show any agonist or antagonist activity for mGluR2, R6 and R7 up to 100 µM. And also, Compound A did not show any agonist or antagonist activity for mGluR5 up to 10 µM.

Taken together, it was proved that the compound A does not have the action upon other groups (Group II and Group III) of metabotropic glutamate.

Regarding mGluR1 α, the compound A dose-dependently inhibited the PI formation induced by 100 µM glutamate, and its $IC_{50}$ value was 24 nM. Also, the $IC_{50}$ value of compound B was 1.7 nM.

Thus, it was confirmed that the method 1 used cerebellar granule cells could be used for the assay of mGluR1 antagonistic activity as an alternative method.

Test Example 2

STZ-induced Diabetes Mice Model

The test was carried out by modifying a previously reported method (*Pharmacol. Biochem. Behav.*, 39, 541–544, 1991). STZ at a dose of 200 mg/kg was intraperitoneally administered to 4-weeks-old ICR mice. A pre-drug tail pinch test was carried out in the afternoon at the fourteenth day after the STZ-administration, and animals showing a reaction latency of 3 seconds or less were subjected to the next day's test. At the fifteenth day after the STZ-administration, each drug was administered orally and a post-drug tail pinch test was carried out 45 minutes after the drug administration.

In this connection, normal mice without STZ-treatment showed an average reaction latency of 6 to 7 seconds in this test. Regarding the STZ-treated mice used in this test, animals which showed a distinct reduction of pain threshold, i.e. animals with a reaction latency of 3 seconds or less were used in the evaluation of drugs.

Statistical analysis was performed with Steel test between the control group and drug-administered group (* and ** in the table are as follows; *p<0.05, **p<0.01 vs. control group).
(Results)

Figure 2:
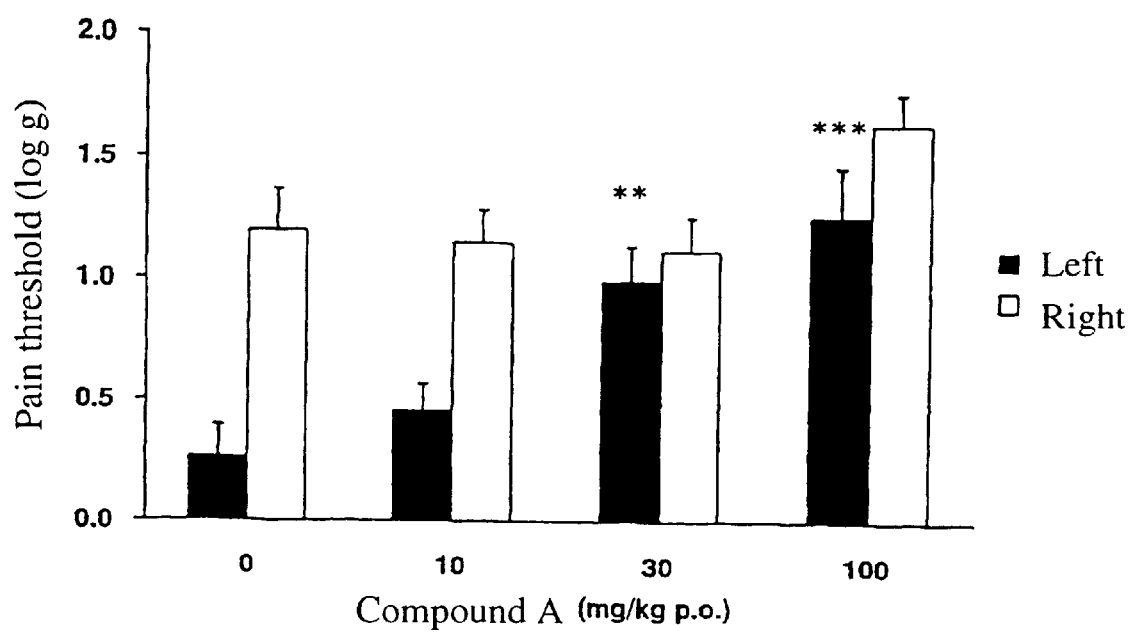
FIG. 2 is a graph showing a result of the measurement of pain threshold when the compound A was administered to spinal L5/L6 nerve-ligated rats.

The compound A significantly prolonged the reaction latency at 30 mg/kg po as shown in FIG. 1A and FIG. 1B, and the compound B significantly prolonged the latency at 10 mg/kg po as shown in FIG. 2.

Thus, it was confirmed that compounds having mGluR1 antagonistic activity have a therapeutic effect for neuropathic pain caused by diabetes mellitus.

Test Example 3

Spinal L5/L6 Nerve-ligated Rats

The test was carried out by modifying a previously reported method (*Pain*, 50, 355–363, 1992). SD rats were used. The left side lumbar nerves (L5 and L6) of each animal were ligated with silk threads under pentobarbital anesthesia. The following test was carried out 7 days after the operation.

After 45 minutes of oral administration of drug, von Frey hair (VFH) test was carried out to measure a mechanical pain threshold. The measurement was carried out on both hindpaws.

Although there was little difference in the mechanical pain thresholds between the left and right hindpaw in sham-operated rats in which the threshold was 17 to 20 g (log(g): 1.23–1.30), the obvious reduction of the mechanical pain threshold in the operated side hinpaw was found in spinal L5/L6 nerve-ligated rats.

Statistical analysis was performed with Dunnet test and carried out on each side hindpaw between the control group and drug-administered groups ( and * in the table are as follows; p<0.01, *p<0.001 vs. control group).
(Results)

Results of the VFH test are shown in FIG. 2. The compound A improved lowered mechanical pain thresholds in the operated side hindpaw at 30 or 100 mg/kg po.

Thus, it was confirmed that a compound having mGluR1 antagonistic activity has a therapeutic effect for neuropathic pain caused by nerve compression.

As a result of these test examples, it was confirmed that compounds having selective and potent antagonistic activity for mGluR1 are useful as therapeutic agents for various types of neuropathic pain.

Production examples of the compounds A and B used in the invention are shown below. Production Example 1
6-Amino-N-cyclohexyl-N, 3-dimethylthiazolo[3,2-a] benzoimidazole-2-carboxamide dihydrochloride (compound A)

The title compound can be synthesized by the method described in Production Method 1 of WO 99/44639.

A THF (80 ml)-methanol (30 ml) solution of N-cyclohexyl-N,3-dimethyl-6-nitrothiazolo[3,2-a] benzoimidazole-2-carboxamide (5.35 g) was mixed at room temperature with aqueous solution (50 ml) of sodium hydrosulfite (12.5 g) and stirred at the same temperature for 12 hours. Next, this was mixed with concentrated hydrochloric acid (10 ml) and heated under reflux for 1 hour. Subsequently, THF and methanol were evaporated under a reduced pressure, and the residue was diluted with water and then neutralized with 28% aqueous ammonia. After extraction with ethyl acetate, the extract was washed with water and saturated brine and dried with anhydrous sodium sulfate, and then the solvent was evaporated under a reduced pressure. The residue was purified by a column chromatography (eluent; chloroform:methanol=20:1), converted into hydrochloride and then recrystallized from methanol-ethyl acetate, thereby obtaining the title compound (3.78 g) as light brown crystals.

NMR: (DMSO-$d_6$, TMS internal standard); δ: 8.11 (d, 1H), 7.84 (d, 1H), 7.41 (dd, 1H), 4.94 (br), 3.80–4.20 (br, 1H), 2.94 (s, 3H), 2.71 (s, 3H), 1.50–1.85 (m, 7H), 1.22–1.40 (m, 2H), 1.02–1.18 (m, 1H). MS (FAB): 343 (M+1).

Production Example 2

Compound B (+)-(1R,2S)-6-Amino-N-methyl-N-(2-methylcyclohexyl) thiazolo[3,2-a]benzoimidazole-2-carboxamide Dihydrochloride Under ice-cooling, fuming nitric acid (0.28 ml) was added to concentrated sulfuric acid (22 ml) solution of (+)-(1R,2S)-N-methyl-N-(2-methylcyclohexyl)thiazolo [3,2-a] benzoimidazole-2-carboxamide (2.2 g) and the mixture was stirred at the same temperature for 30 minutes. The reaction solution was poured into ice water and neutralized with a 28% aqueous ammonia solution and then the resulting precipitate was collected by filtration to obtain (1R,2S)-N-methyl-N-(2-methylcyclohexyl)-6-nitrothiazolo [3,2-a] benzoimidazole-2-carboxamide. This was treated in the same manner as in Production Example 1 to obtain the title compound (242 mg).

$[\alpha]^{25}_D$=+17.08° (c 0.24, EtOH) NMR: (DMSO-$d_6$, TMS internal standard); δ: 9.16 (s, 1 H), 8.15 (s, 1 H), 7.81 (d, 1 H), 7.42 (dd, 1 H), 4.85 (br), 4.25–4.38 (m, 1 H), 3.26 (s, 3 H), 1.30–2.35 (m, 9 H), 1.01 (d, 3 H). MS (FAB): 343 (M+1).

Industrial Applicability

According to the present invention, compounds having mGluR1 antagonistic activity have a therapeutic effect on the lowered pain threshold in various types of neuropathic pain with their systemic administration, so that they are useful as pharmaceuticals for neuropathic pain, which are easy for patients to take and have efficient therapeutic effect with less side effects.

What is claimed is:

1. A pharmaceutical composition for use in treating neuropathic pain, which is administered by a systemic method of administration and which comprises a compound having mGluR1 antagonistic activity, wherein the compound having mGluR1 antagonism is a compound selected from 6-amino-N-cyclohexyl-N, 3-dimethylthiazolo[3,2-a] benzoimidazole-2-carboxamide dihydrochloride and (+)-(1R,2S)-6-amino-N-methyl-N-(2-methylcyclohexyl) thiazolo[3,2-a]benzoimidazole-2-carboxamide dihydrochloride.

2. The pharmaceutical composition according to claim 1, wherein the neuropathic pain is induced by diabetes or compression of nerves.

3. The pharmaceutical composition according to claim 1, wherein the neuropathic pain is induced by diabetes.

4. The pharmaceutical composition according to claim 1, wherein the systemic administration method is oral administration.

* * * * *